United States Patent [19]

Wegleitner et al.

[11] 4,278,794

[45] Jul. 14, 1981

[54] PROCESS FOR PREPARING PURE CYANURIC ACID

[75] Inventors: Karlheinz Wegleitner, Linz; Wilfried Krulla, Traun; Richard Willim, Linz, all of Austria

[73] Assignee: Chemie Linz Aktiengesellschaft, Linz, Austria

[21] Appl. No.: 165,154

[22] Filed: Jul. 1, 1980

[30] Foreign Application Priority Data

Jul. 19, 1979 [DE] Fed. Rep. of Germany ....... 2929211

[51] Int. Cl.$^3$ .......................................... C07D 251/32
[52] U.S. Cl. ................................................... 544/192
[58] Field of Search ......................................... 544/192

[56] References Cited

U.S. PATENT DOCUMENTS

| 3,563,987 | 2/1971 | Berkowitz | 544/192 |
|---|---|---|---|
| 3,761,474 | 9/1973 | Mesiah | 544/192 |
| 3,886,153 | 5/1975 | Berkowitz | 544/192 |
| 3,996,225 | 12/1976 | Gray et al. | 544/192 |
| 4,029,660 | 6/1977 | Berkowitz | 544/192 |
| 4,031,091 | 6/1977 | Berkowitz et al. | 544/192 |

*Primary Examiner*—John M. Ford
*Attorney, Agent, or Firm*—Mark Dryer

[57] ABSTRACT

Pure cyanuric acid is prepared from crude or waste melamine by introducing the melamine into 70 to 80% strength sulfuric acid at room temperature and heating the reaction mixture to 150° to 190° C., the water introduced with the sulfuric acid being distilled off during the heating period.

3 Claims, No Drawings

PROCESS FOR PREPARING PURE CYANURIC ACID

BACKGROUND OF THE INVENTION

The present invention relates to a process for the preparation of pure cyanuric acid from crude or waste melamine, which, in particular, contains ammeline and ammelide, using sulfuric acid.

Most of the processes for the preparation of cyanuric acid are based on the pyrolysis of urea, and a more or less highly contaminated end product is obtained which has to be purified before it can be put to further use.

Hitherto, only two processes have been disclosed which yield cyanuric acid from melamine or ammeline or ammelide as the starting material, using sulfuric acid.

U.S. Pat. No. 2,768,167 discloses a process for the preparation of cyanuric acid from melamine, ammeline, the ammeline:ammelide complex or mixtures thereof, according to which sulfuric acid maintained in a stoichiometric excess of up to 5% of free acid supplied as an aqueous solution thereof having a concentration of at least 5%, preferably 10 l to 20%, free acid is used as the mineral acid the hydrolysis is carried out at a temperature of at least 175° C. under at least the autogenously developed pressure. Temperatures of 180° to 200° C. are preferred.

As has been found on repeating the Examples of U.S. Pat. No. 2,768,187, the said process can be carried out only when, as, say, in Example 1 of U.S. Pat. No. 2,768,187, the reaction is carried out with amounts of sulfuric acid which are substantially higher than those claimed. The molar ratio of melamine to sulfuric acid is 1:3.96 in the said Example. If, however, it is attempted to react melamine in an analogous manner to a mixture of ammeline and ammelide with 20% strength sulfuric acid by the procedure of Example 3 of U.S. Pat. No. 2,768,187, the molar ratio of sulfuric acid to the amino groups present to be 0.52, corresponding to the patent claims, the cyanuric acid obtained is not pure but, even after hydrolyzing for one hour instead of for the 10 to 20 minutes indicated, is only crude cyanuric acid containing about 15% of impurities.

According to a more recent process (Japan Kokai No. 1975, 32,193), the conversion of melamine, melamine-containing residues or melamine cyanurate to cyanuric acid is carried out with dilute mineral acid, for example sulfuric acid, and the reaction, although under normal pressure, must be carried out in two stages in order to obtain pure cyanuric acid. Ammeline salts are initially obtained in the first stage and these have to be further hydrolyzed to cyanuric acid in the second stage.

Surprisingly, it has now been found that cyanuric acid in a purity of more than 99% may be obtained from ammeline-containing and/or ammelide-containing crude or waste melamine by reaction with relatively highly concentrated sulfuric acid without adverse decomposition phenomena in a one-stage process under normal pressure.

SUMMARY OF THE INVENTION

Thus according to the present invention there is provided a process for the preparation of pure cyanuric acid which comprises hydrolyzing crude or waste melamine with sulfuric acid by introducing the crude or waste melamine, at room temperature, with stirring, into 70 to 80% strength sulfuric acid in the equivalent amount for formation of ammonium bisulfate, heating the reaction mixture under normal pressure to a temperature within the range of 150° to 190° C. over a period of 1 to 2 hours, whilst distilling off the water introduced with the sulfuric acid, and subsequently adding water, cooling the reaction mixture to room temperature, and isolating the pure cyanuric acid product by crystallizing out and filtering off the cyanuric acid, suspending the filtered product in water and filtering again.

Sulfuric acid concentrations from 70 to 75% and reaction temperatures of 160°–190° C. are preferred. With regard to the sulfuric acid concentration according to the invention, it must be stated that at concentrations higher than about 80% there is a danger that the reaction will become too vigorous if the efficiency of the cooling is not optimum and, as a result, decomposition of the triazine ring can arise. At concentration below 70%, the reaction time, which in the case of the reaction temperatures according to the invention is generally 3 to 5 hours, is prolonged in a disadvantageous manner.

It is surprising, in contrast to the processes known hitherto that it is not necessary to use dilute sulfuric acid of up to about 20% strength as the starting material in order to obtain a pure product, but that relatively highly concentrated acid may be employed under normal pressure in a one-stage process without the yield suffering because of decomposition of the starting material or end product to give ammonia and carbon dioxide. Temperatures which are above or below the temperature range according to the invention have the same effect on the yield and the reaction time as sulfuric acid concentrations which are above or below those according to the invention. The optimum reaction time is a consequence of the sulfuric acid concentration and the reaction temperature and may be determined easily from case to case. Distilling off the water, introduced with the sulfuric acid, in the course of 1 to 2 hours is necessary because if the temperature falls below the reaction temperature the reaction time is unnecessarily prolonged. The crude or waste melamine is introduced into the sulfuric acid, since the reaction is highly exothermic and the reaction temperature may be better controlled in this way.

After the reaction has ended water is added in an amount such that the ammonium bisulfate formed remains in solution, in order to prevent precipitation of the ammonium bisulfate on cooling. Suspending the cyanuric acid which has been filtered off and filtering off again increases the purity of the acid.

Cyanuric acid derivatives are used as disinfectants and as additives to PVC plasticizers, vinyl polymers, epoxide resins and others.

The following Examples illustrate the process according to the invention in more detail.

EXAMPLE 1

736 g. Of 80% strength sulfuric acid is initially introduced into a glass flask with a reflux condenser, and 252 g. of approximatley 97% pure crude melamine is introduced, with stirring. The temperature is raised to the boiling point, which is at 160° C., in the course of one hour. If the temperature should rise too sharply, cooling may be carried out with compressed air. The solution, which initially is clear, is kept at the boil for four hours. If the resulting suspension should become too viscous, a few ml. of water is added. After the hyrolysis has ended, 810 ml of water is added, the mixture is cooled to room temperature and the cyanuric acid is filtered off after it has crystallized out. It is suspended in water, the suspension is stirred and the product is filtered off again and washed. This gives 243 g. of cyanuric acid (94.2% based on the crude melamine employed) with an ammelide content of less than 0.3%.

If the filtrate is to be free from cyanuric acid, 1,250 ml. of water is added after the hydrolysis has ended. Whilst cooling, ammonia is passed in until the pH is 6. After cooling to room temperature, the cyanuric acid is filtered off and washed as indicated above, 245 g (95.0%) of cyanuric acid with an ammelide content of less than 0.3% being obtained. The ammonium sulfate solution is heated to the boil and treated with a stoichiometric amount of melamine, by which means the cyanuric acid present is precipitated as melamine cyanurate. The resulting melamine cyanurate may be recycled for hydrolysis and the ammonium sulfate solution is virtually free from organic impurities. Melamine cyanurate also may be utilized, for example, as flame retardant.

EXAMPLE 2

333 kg Of 70% strength sulfuric acid is initially introduced into an enamel kettle and 100 kg of a waste melamine which contains ammeline and ammelide and has a melamine content of about 95% is added, with stirring, the temperature rising to about 90° C. This suspension is heated to the boiling point of 132° C. and is then heated up to 160° C. in the course of one hour, whilst distilling off water. The suspension is kept at the boil under reflux, at 160° C. for 4 hours and 310 l. of water is then added, the temperature falling to 120° C. After cooling to room temperature, the cyanuric acid is centrifuged off, washed and suspended in water, using a weight ratio of 1 part of cyanuric acid to 2 parts of water, the suspension is stirred for one hour at room temperature and the cyanuric acid is centrifuged off and washed. About 96 kg. (93.9%) of a cyanuric acid with an ammelide content of less than 0.3% is obtained. The ammonium bisulfate impurity amounts to about 0.03%. Melamine and ammeline are not detectable.

If the solution is heated to 190° C. in the course of two hours instead of to 160° C. in the course of one hour, the reaction time after the boiling point at 190° C. is reached is shortened to about one and a half hours. In order to improve the stirability, it is advantageous to add a little water several times, but the boiling point which has been set up should not be lowered by these additions.

We claim:

1. In a process for the preparation of pure cyanuric acid by hydrolyzing crude or waste melamine using sulfuric acid as a hydrolyzing agent, the improvement which comprises introducing the crude or waste melamine, at room temperature, with stirring, into 70 to 80% strength sulfuric acid in the equivalent amount for formation of ammonium bisulfate, heating the reaction mixture under normal pressure to a temperature within the range of 150° to 190° C. over a period of 1 to 2 hours, whilst distilling off the water introduced with the sulfuric acid, and subsequently adding water, cooling the reaction mixture to room temperature, and isolating the pure cyanuric acid product by crystallizing out and filtering off the cyanuric acid, suspending the filtered product in water and filtering again.

2. A process according to claim 1, in which the sulfuric acid concentration is 70 to 75%.

3. A process according to claim 1, in which the reaction temperature is from 160° to 190° C.

* * * * *